United States Patent
Chang et al.

(10) Patent No.: US 10,772,922 B2
(45) Date of Patent: Sep. 15, 2020

(54) METHODS OF TREATING OR PREVENTING VIRAL INFECTION BY USING PLANT EXTRACTS

(71) Applicants: NATIONAL TAIWAN UNIVERSITY, Taipei (TW); TAICHUNG DISTRICT AGRICULTURAL RESEARCH AND EXTENSION STATION, COUNCIL OF AGRICULTURE, EXECUTIVE YUAN, Changhua County (TW)

(72) Inventors: Luan-Yin Chang, Taipei (TW); Yu-Hsin Chen, Changhua County (TW)

(73) Assignees: NATIONAL TAIWAN UNIVERSITY, Taipei (TW); TAICHUNG DISTRICT AGRICULTURAL RESEARCH AND EXTENSION STATION, COUNCIL OF AGRICULTURE, EXECUTIVE YUAN, Changhua County (TW)

( * ) Notice: Subject to any disclaimer, the term of this patent is extended or adjusted under 35 U.S.C. 154(b) by 0 days.

(21) Appl. No.: 15/803,436

(22) Filed: Nov. 3, 2017

(65) Prior Publication Data
US 2018/0125908 A1    May 10, 2018

Related U.S. Application Data
(60) Provisional application No. 62/419,312, filed on Nov. 8, 2016.

(30) Foreign Application Priority Data
Aug. 23, 2017 (TW) ............................... 106128647 A

(51) Int. Cl.
*A61K 36/537* (2006.01)
*A61K 36/28* (2006.01)

(52) U.S. Cl.
CPC ............ *A61K 36/28* (2013.01); *A61K 36/537* (2013.01); *A61K 2236/331* (2013.01); *A61K 2300/00* (2013.01)

(58) Field of Classification Search
None
See application file for complete search history.

(56) References Cited

U.S. PATENT DOCUMENTS
2013/0028995 A1 * 1/2013 Shrivastava ........... A61K 36/18 424/729
2016/0151436 A1 * 6/2016 Squires .................. A61K 36/28 424/400

FOREIGN PATENT DOCUMENTS
KR    2013 123947 A  *  11/2013

OTHER PUBLICATIONS

Vimalanathan S. et al. Antiinflammatory Activites of Echinacea Extracts do not Correlate With Traditional Marker Components. Pharmaceutical Biology 47(5)430-435, 2009. (Year: 2009).*
Sperber S. et al. Echinacea purpurea for Prevention of Experimental Rhinovirus Colds. Clinical Infectious Diseases 38(1)1367-71, 2004. (Year: 2004).*
Hudson J. et al. Characterization of Antiviral Activities in Echinacea Root Preparations. Pharmaceutical Biology 43(9)790-6, 2005. (Year: 2005).*
Hudson, J. et al. Antiviral Activities of Herbal Preparations. Planta Medica 76(12)abstract P492, Aug. 2010. (Year: 2010).*
Zhao S. et al. Interferon Plus Chinese Herbs are Associated with Higher Sustained Biological Response . . . Antiviral Research 89(2) 156-164, Feb. 2011. (Year: 2011).*
Cheng et al., Putranjivain A from Euphorbia jolkini inhibits both virus entry and late stage replication of herpes simplex virus type 2 in vitro, The Journal of antimicrobial chemotherapy Apr. 2004, 53, pp. 577-583.
Sharma et al., "Induction of multiple pro-inflammatory cytokines by respiratory viruses and reversal by standard Echinacea, a potent antiviral herbal extract", pp. 165-170, 2009, Antiviral Research, www.elsevier.com/locate/antiviral.

* cited by examiner

*Primary Examiner* — Ralph J Gitomer
(74) *Attorney, Agent, or Firm* — WPAT, PC

(57) ABSTRACT

Provided is a method of treating or preventing adenovirus and enterovirus infection by administering an antiviral composition that contains an *Echinacea purpurea* extract, a *Salvia miltiorrhiza* extract, or combinations thereof. The antiviral composition blocks adenoviruses and enterovirus infection through virucidal activity against adenovirus and inhibition of adenovirus and enterovirus attachment to and penetration into cells. Also provided is a method of preparing the antiviral composition.

7 Claims, 12 Drawing Sheets

METHODS OF TREATING OR PREVENTING VIRAL INFECTION BY USING PLANT EXTRACTS

CROSS-REFERENCES TO RELATED APPLICATIONS

This application claims priority of Provisional Application No. 62/419,312, filed on Nov. 8, 2016 and Taiwan patent application No. 106128647, filed on Aug. 23, 2017, the content of which is incorporated herein in its entirety by reference.

BACKGROUND OF THE INVENTION

1. Field of the Invention

The present invention relates to methods of treating viral infection and preparing an antiviral composition using plant extracts. Particularly, the present invention relates to methods of treating viral infection using extracts of Echinacea purpurea and Salvia miltiorrhiza and preparation of an antiviral composition containing those extracts.

2. The Prior Art

Enterovirus 71 (referred to as EV71) has been associated with outbreaks in the United States, Europe, Australia, Japan, Brazil and Malaysia, since it was originally recognized in California in 1969. Before 1998, three large outbreaks with dozens of fatal cases occurred in Bulgaria, Hungary, and Malaysia in 1975, 1978 and 1997, respectively. In the last century, the largest and most severe EV71 epidemic exploded in Taiwan in 1998. A total of 129,106 cases of hand-foot-and-mouth disease and herpangina were reported, 405 cases had severe neurologic complications and/or pulmonary edema, and 78 children died. In this century, EV71 continues to circulate in Taiwan as well as in the other Asian countries and contributes to huge disease burden. For example, in mainland China, EV71 has caused several hundreds to thousands of fatal cases each year since 2007; in Vietnam, dozens to several hundreds of fatal EV71 cases sometimes occurred (in 2005, 2007, 2009, and 2011). Although stage-based management for severe EV71 infections was developed in Taiwan, the case-fatality was lower while most survivors of brainstem encephalitis plus cardiopulmonary failure might have neurologic sequelae and impaired cognition. Recent follow-up studies further demonstrated that EV71 central nervous system (CNS) infection could cause long-term sequelae including neurological development and cognitive function, and could also increase the risk of attention deficit and hyperactivity disorder (ADHD). Continuous EV71 disease and laboratory surveillance is warranted to allow for possible earlier control and prevention measures. However, there is no available EV71-specific antiviral drug now.

Human adenovirus has more than fifty serotypes, and it frequently causes respiratory diseases in children and severe infectious disease in transplant or immunocompromised patients and sometimes even in immunocompetent adults. Because adenovirus spreads with droplet, it is easily transmitted among children and causes outbreaks at schools or kindergartens. According to statistics of Centers for Disease Control in Taiwan, human adenovirus was the most common respiratory virus and circulated all year round in Taiwan. Recently, adenovirus type 3 and type 7 caused community outbreak in Taiwan and caused acute respiratory failure and fatal cases, younger or patients with underlying diseases such as neurological diseases tend to develop severe and even fatal diseases. Therefore, infection of adenovirus leads to children's heavy disease burden and worrisome complications.

There is lack of commercially available antiviral drugs specific for the treatment of adenoviruses and enterovirus 71. Therefore, it is of utmost importance to develop a safe and effective medicine to treat or prevent the serious diseases caused by both enterovirus 71 and adenoviruses.

SUMMARY OF THE INVENTION

In one aspect, the present invention provides a method of treating or preventing a viral infection, including administering to a subject in need thereof an effective amount of an antiviral composition, wherein the antiviral composition includes an Echinacea purpurea extract, a Salvia miltiorrhiza extract, or combinations thereof. The viral infection includes adenovirus infection and may further include enterovirus infection.

In one embodiment of the invention, the adenovirus infection is caused by one selected from the group consisting of human adenovirus type 1 (referred to as HAdV1), human adenovirus type 2 (referred to as HAdV2), human adenovirus type 3 (referred to as HAdV3), human adenovirus type 4 (referred to as HAdV4), human adenovirus type 7 (referred to as HAdV7), and the enterovirus infection is caused by enterovirus 71.

In another embodiment of the invention, the E. purpurea extract is prepared by extraction of E. purpurea with water or a water-alcohol mixture, preferably by extraction from an aerial part of dried E. purpurea; the S. miltiorrhiza extract is prepared by extraction of S. miltiorrhiza, such as extraction from a root or a rhizome of S. miltiorrhiza, with water or a water-alcohol mixture. The water-alcohol mixture includes 1-95% v/v ethanol.

In another embodiment of the invention, the antiviral composition includes a water extract of E. purpurea and a 70% ethanol extract of S. miltiorrhiza at a weight ratio ranging from 1:9 to 9:1, preferably at a weight ratio of 3:7.

In yet another embodiment of the invention, the E. purpurea extract can inhibit the attachment of an adenovirus and an enterovirus to a cell and inhibit the penetration of the adenovirus into the cell. The E. purpurea extract also deactivates the adenovirus.

In still another embodiment of the invention, the S. miltiorrhiza extract can inhibit the attachment of an adenovirus and an enterovirus to a cell and also inhibit the penetration of the adenovirus and the enterovirus into the cell.

In another aspect, the present invention provides a method of preparing an antiviral composition, including the steps of: (a) extracting Echinacea purpurea with water or a water-alcohol mixture to obtain an E. purpurea extract, (b) extracting Salvia miltiorrhiza with water or a water-alcohol mixture to obtain a S. miltiorrhiza extract; and (c) mixing the E. purpurea extract and the S. miltiorrhiza extract at a specific ratio to obtain the antiviral composition.

In one embodiment of the invention, the E. purpurea extract in step (a) is prepared by water extraction of dried E. purpurea at a temperature starting from 95° C. or higher and decreasing to 60-80° C., and the weight ratio of the dried E. purpurea to water ranges from 1:5 to 1:20; the S. miltiorrhiza extract in step (b) is prepared by extraction with a 70% ethanol aqueous solution at a temperature of 10° C.-60° C., and the weight to volume ratio of S. miltiorrhiza to the 70% ethanol aqueous solution ranges from 1:5 to 1:10; a water extract of *E. purpurea* and a 70% ethanol extract of *S. miltiorrhiza* is mixed in step (c) at a weight ratio ranging from 1:9 to 9:1, preferably at a weight ratio of 3:7.

The present invention discloses a safe and effective antiviral composition prepared from the *E. purpurea* extract, the *Salvia miltiorrhiza* extract, or combinations thereof, and therefore offers a strategy to inhibit adenovirus and enterovirus infection. The antiviral composition blocks or reduces adenovirus and enterovirus infection by multi-target antiviral mechanisms, including virucidal activity against adenovirus and inhibition of adenovirus and enterovirus attachment to and penetration into cells. Thus, the antiviral composition has the potential for preventing or treating diseases associated with viral infection in a subject, and it also lowers the possibility of drug resistance.

The present invention is further explained in the following drawings and examples. It is understood that the examples given below do not limit the scope of the invention, and it will be evident to those skilled in the art that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Figure 1A:
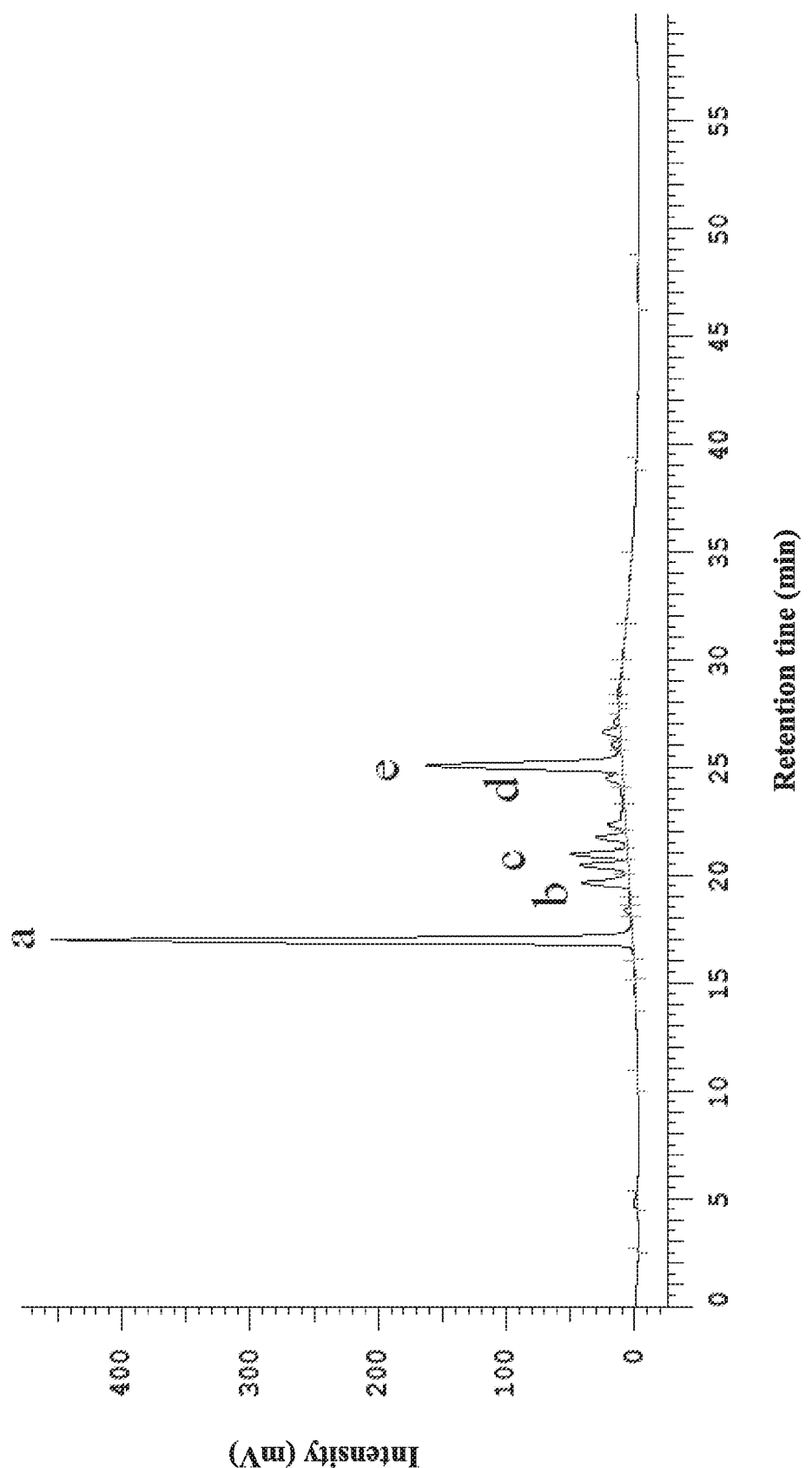
FIG. 1A shows a high performance liquid chromatography (HPLC) chromatogram of an *E. purpurea* water extract at detection wavelength of 330 nm; peak a represents caftaric acid (17.0 min), peak b represents chlorogenic acid (19.6 min), peak c represents cynarin (21.0 min), peak d represents echinacoside (22.4 min), and peak e represents cichoric acid (25.1 min)

The present invention provides a method of treating or preventing viral infection, including administering to a subject in need thereof an effective amount of an antiviral composition, wherein the antiviral composition contains an *E. purpurea* extract, a *S. miltiorrhiza* extract, or combinations thereof, and the viral infection includes adenovirus and enterovirus infection. The present invention also provides a method of preparing the abovementioned antiviral composition. The following examples illustrate the process of extracting *E. purpurea* and *S. miltiorrhiza* with water or a water-alcohol mixture. Also disclosed are data supporting the antiviral activity and non-cytotoxicity of the *E. purpurea* extract, the *S. miltiorrhiza* extract, and combinations thereof at various ratios based on plaque assay and cytotoxicity assay, respectively. Furthermore, according to the results of virucidal assay, attachment assay, and penetration assay, the antiviral composition of the present invention exerts antiviral activity through mechanisms including deactivation of adenovirus, inhibition of adenovirus and enterovirus attachment to cells, and inhibition of adenovirus penetration into cells due to the *E. purpurea* extract, and inhibition of adenovirus and enterovirus attachment to and penetration into cells due to the *S. miltiorrhiza* extract.

Definition

Numerical quantities given herein are approximate, and experimental values may vary within 20 percent, preferably within 10 percent, and most preferably within 5 percent. Thus, the terms "about" and "approximately" refer to within 20 percent, preferably within 10 percent, and most preferably within 5 percent of a given value or range.

As used herein, the term "water extract" refers to a composition obtained by extraction of plant materials in the form of slices, chunks, granules, or powders using water as a solvent. The water extract may be processed into the form of solid or liquid.

As used herein, the term "% alcohol extract" refers to a composition obtained by extraction of plant materials in the form of slices, chunks, granules, or powders using a water-alcohol mixture as a solvent. The water-alcohol mixture includes alcohol at a predetermined percentage. The % alcohol extract may be processed into the form of solid or liquid.

Methods and Materials
Cell Culture and Virus Preparation

The cells used in the examples were purchased from American Type culture collection (ATCC). These cells include Vero cell lines from African green monkey kidney epithelial cells (ATCC CCL-81), human adenocarcinomic A549 cells (ATCC CCL-185), and human rhadomyosarcoma (RD) cells (ATCC CCL-136). Vero cells and A549 cells were cultured in minimum essential medium (MEM; Hyclone) supplemented with Earle's Balanced Salts, 10% heat-inactivated fetal bovine serum (FBS), and 1% Penicillin-Streptomycin-Amphotericin B solution. RD cells were cultured in Dulbeco's Modified Eagle Medium (DMEM; Hyclone) supplemented with 10% heat-inactivated FBS and 1% Penicillin-Streptomycin-Amphotericin B solution. All cells were incubated at 37° C. in a humidified atmosphere containing 5% $CO_2$.

Virus Preparation

Human adenovirus type 3 (HAdV3) and the 2847 strain (GenBank: HQ283527) of enterovirus 71 (EV71) were isolated from clinical samples in Taiwan. According to the following steps, HAdV3 and EV71 were amplified using A549 cells and RD cells, respectively. First, cells reaching 80-90% confluence in a flask were rinsed with phosphate buffered saline (referred to as PBS; 137 mM sodium chloride, 2.7 mM potassium chloride, 10 mM sodium hydrogen phosphate, and 1.8 mM potassium dihydrogen phosphate, pH 7.4) after the medium was discarded. A diluted virus solution was then added to cover all the cells for infection in a cell incubator (37° C., 5% $CO_2$) for 2 hours, during which the flask was shaken once every 30 minutes. After the infection, the virus solution was removed, and the cells were rinsed with PBS once and fed with complete medium containing 2% FBS. The cells were cultured in the cell incubator until more than 70% of the cells exhibited cytopathic effect. Afterwards, the culture was centrifuged (2500 rpm, 4° C., 20 min), and the cells infected by virus and a supernatant were collected separately. The cells in a little of the supernatant were disrupted and the intracellular virus particles were released by three freeze-thaw cycles using liquid nitrogen and a 37° C. water bath. The cell lysates were centrifuged (2500 rpm, 4° C., 20 min) to collect a supernatant, which was then mixed with the supernatant previously obtained to prepare a virus solution containing virus particles. Titers of the virus solutions were determined by plaque assay with Vero cells and were expressed as plaque-forming units (PFU) per mL. Virus stocks were stored at −80° C. until use.

Plaque Assay

Plaque reduction assay was performed to test the antiviral activity of plant extracts, including the *E. purpurea* extract and the *S. miltiorrhiza* extract. In brief, Vero cells were seeded into a 6-well culture plate at a density of $4\times10^5$ cells/well and incubated at 37° C. with 5% $CO_2$ overnight. Next day, 50-100 PFU of virus and different dilutions of plant extracts were mixed to a final volume of 500 μL and incubated at 37° C. for 2 hours, and then the mixture were added to the cells in each well of the 6-well culture plate for another 2-hour incubation at 37° C. The mixture was removed from the 6-well culture plate and 2 mL MEM containing 2% FBS, 1% 2-[4-(2-hydroxyethyl)piperazin-1-yl]ethanesulfonic acid (HEPES), 1% Penicillin-Streptomycin-Amphotericin B, and 0.3% agarose was added to each well. After incubation of the 6-well culture plate at 37° C. for 5-7 days, the cells were fixed with 10% formaldehyde for at least 1 hour and stained with 0.05% crystal violet to count virus plaques. Inhibition of virus replication by the plant extracts was calculated according to the following formula:

$$[1-(VD/VC)]\times 100\%$$

VD: the number of virus plaque in the presence of the plant extract
VC: the number of virus plaque in the absence of the plant extract The minimal concentrations of the plant extracts required to reduce the number of viral plaques by 50% and 90% were referred to as IC50 and IC90, respectively, and were calculated by regression analysis of the dose-response curves based on plaque assays.

Cytotoxicity Assay and Selective Index

To investigate the effects of the plant extracts on cell viability, XTT (2,3-Bis-[2-Methoxy-4-Nitro-5-Sulfophenyl]-2H-Tetrazolium-5-Carboxanilide inner salt) assay was performed. Briefly, $3\times10^4$ Vero cells/well were seeded into a 96-well culture plate and incubated at 37° C. with 5% $CO_2$ overnight. Next day, 100 μL different dilutions of the plant extracts were added into each well. After incubation of the 96-well culture plate at 37° C. for 2 days, a reconstituted XTT stock solution in an amount equal to 20% of the culture medium volume was added. After the 96-well culture plate was incubated at 37° C. for 3 hours, the absorbance of each well at 450 nm and 650 nm was measured. The absorbance of test samples and the absorbance of solvent control were first calculated by subtracting the absorbance at 650 nm from that at 450 nm, and then cytotoxicity of the plant extracts at different concentrations was calculated according to the following formula and expressed as cytotoxicity percentage:

$$[1-(At/As)]\times 100\%$$

At: the absorbance of test samples
As: the absorbance of solvent control

The 50% cytotoxicity concentration (CC50) of the plant extracts, defined as the concentration of the plant extracts required to reduce cell viability by 50%, was derived from the abovementioned cytotoxicity percentage. The selective index (SI) was calculated as CC50/IC50.

Virucidal Assay

Virucidal assay was performed based on the procedure described in Cheng et al (Cheng H Y, Lin T C, Yang C M, Wang K C, Lin L T, Lin C C, J Antimicrob Chemother. 2004 April; 53(4):577-583) with minor modification. The virus solution containing HAdV3 or EV71 was mixed with various concentrations of the plant extracts for 2 hours at 37° C., and the residual infectivity of each of the mixtures was determined by plaque assay.

Attachment Assay

The attachment assay was performed based on the procedure described in Cheng et al (Cheng H Y, Lin T C, Yang C M, Wang K C, Lin L T, Lin C C, J Antimicrob Chemother. 2004 April; 53(4):577-583) with minor modification. To investigate whether the plant extracts have any effect on viral attachment, Vero cell monolayer, seeded into a 6-well culture plate at a density of $4\times10^5$ cells/well, was pre-chilled at 4° C. for 1 hour, and then infected with virus in the absence or presence of serial dilutions of the plant extract. The cells were incubated with virus at 4° C. for 2 hours. Afterwards, the infected Vero cell monolayer was washed three times with cold PBS. The cells were then overlaid with MEM containing 2% FBS, 1% HEPES, 1% Penicillin-Streptomycin-Amphotericin B, and 0.3% agarose and incubated at 37° C. for 5-7 days in order for plaque assay which was performed to determine the inhibitory effect of the plant extracts on viral attachment.

Penetration Assay

The penetration assay was performed based on the procedure described in Cheng et al (Cheng H Y, Lin T C, Yang C M, Wang K C, Lin L T, Lin C C, J Antimicrob Chemother. 2004 April; 53(4):577-583) with minor modification. To investigate whether the plant extracts have any effect on viral entry, Vero cell monolayer, seeded into a 6-well culture plate at a density of $4 \times 10^5$ cells/well, was pre-chilled at 4° C. for 1 hour and then infected with virus. The cells were incubated with virus at 4° C. for 2 hours to allow viral attachment. Afterwards, the plant extract was added to the infected Vero cell monolayer and the culture was incubated at 37° C. to maximize viral penetration. In contrast, the control cells were not treated with the plant extracts. At 10 min intervals, the infected Vero cell monolayer was treated with acidic PBS (pH 3) for 1 minute to inactivate non-penetrated virus. PBS at pH 11 was then immediately added to neutralize the acidic PBS. After the neutral PBS was removed, the cells were overlayed with MEM containing 2% FBS, 1% HEPES, 1% Penicillin-Streptomycin-Amphotericin B, and 0.3% agarose and incubated at 37° C. for 5-7 days in order for plaque assay which was performed to determine the inhibitory effect of the plant extracts on viral penetration.

Example 1

Preparation of the Plant Extracts and Analysis of Indicative Components 1.1 Methods of Preparation This example exemplifies the preparation methods of the plant extracts that are used to prepare the antiviral composition. For the *E. purpurea* extract and the *S. miltiorrhiza* extract, the extraction solvent is water or a water-alcohol mixture. The water-alcohol mixture, as used herein, refers to a mixture of alcohols of any kinds and water, such as a methanol aqueous solution, an ethanol aqueous solution, and a 2-propanol aqueous solution. The water-alcohol mixture may include 1-95% alcohol by volume (v/v). The preparation methods of extracts are similar among various plants. Provided below are steps for preparing an *E. purpurea* water extract and a 70% ethanol extract of *S. miltiorrhiza*, which are examples illustrating the process to obtain the water extracts or the alcohol extracts of the two plants.

For preparation of the *E. purpurea* water extract, the aerial part or root of *E. purpurea* is dried at 45-50° C. to a water content of 8-12% and ground into granules with sizes from about 10 cm to 60 mesh. Upon extraction, the granular material of *E. purpurea* is mixed with water at a weight ratio of 1:5-1:20, preferably at a weight ratio of 1:10. Extraction temperature is first raised to 95° C. or above for sterilization and then cooled down to 60-80° C., at which the material is extracted for 2 hours. The *E. purpurea* water extract is obtained therefrom after two extractions. Furthermore, the extract may be filtered and concentrated at 60-70° C. under reduced pressure. In one embodiment, the solid content of the concentrate is about 38% (w/w). After this extraction process, about 15-20% of the *E. purpurea* material, by dry mass, is extracted.

For preparation of the 70% ethanol extract of *S. miltiorrhiza*, the root or rhizome of fresh *S. miltiorrhiza* was washed and sliced. The sliced material of *S. miltiorrhiza* was then mixed with a 70% ethanol aqueous solution at a weight to volume ratio (w/v) of 1:5-1:10, preferably at a weight to volume ratio of 1:8, and extracted at 10-60° C., preferably at 40-50° C., for 1-2 days. The 70% ethanol extract of *S. miltiorrhiza* is obtained therefrom after two extractions. Furthermore, the extract may be filtered and concentrated. In one embodiment, the solid content of the concentrate is about 1.14% (w/w). After this extraction process, about 10-15% of the *S. miltiorrhiza* material, by dry mass, is extracted.

1.2 Analysis of Indicative Components

To identify the constituents of the *E. purpurea* extract, high performance liquid chromatography (HPLC) was used to analyze the indicative components of the *E. purpurea* water extract described in Example 1.1. The reference standards include phenolic compounds, such as cichoric acid, caftaric acid, chlorogenic acid, cynarin, and echinacoside, and alkamides 8/9. The HPLC system includes a Hitachi L-7100 pump and is equipped with an L-7400 detector and a Mightysil RP-18 GP250-4.6 (5 µm) reversed-phase column (Kanto Chemical Co.) While analysis was carried out, the mobile phase was a combination of a 0.1% phosphoric acid aqueous solution and methanol according to the gradient program shown in TABLE 1; the flow rate was 1.0 mL/min; column temperature was 35° C.; and the detection wavelength for phenolic compounds and alkamides were 330 nm and 260 nm, respectively. Moreover, polysaccharides in the *E. purpurea* water extract were extracted and analyzed based on phenol-sulfuric acid assay published in the AOAC (Association of Official Analytical Communities) method 988.12 for dextran in raw cane sugar. Dextrin solutions at various concentrations were prepared by mixing various amounts of dextrin, which was the reference standard for polysaccharides, and distilled water to a final volume of 400 µL. Each of the dextrin solution was then mixed with 100 µL of a 5% phenol solution (reagent grade), followed by addition of 1 mL sulfuric acid (95-98%) and quick mixing. After heated in boiled water for 2 minutes and cooled down to room temperature, the reaction mixture was analyzed by a full-spectrum ELISA (enzyme-linked immunosorbent assay) microreader at 485 nm.

TABLE 1

| Time (min) | 0 | 10 | 40 | 50 | 60 |
|---|---|---|---|---|---|
| 0.1% phosphoric acid | 100 | 70 | 40 | 0 | 100 |
| methanol | 0 | 30 | 60 | 100 | 0 |

Figure 1B:
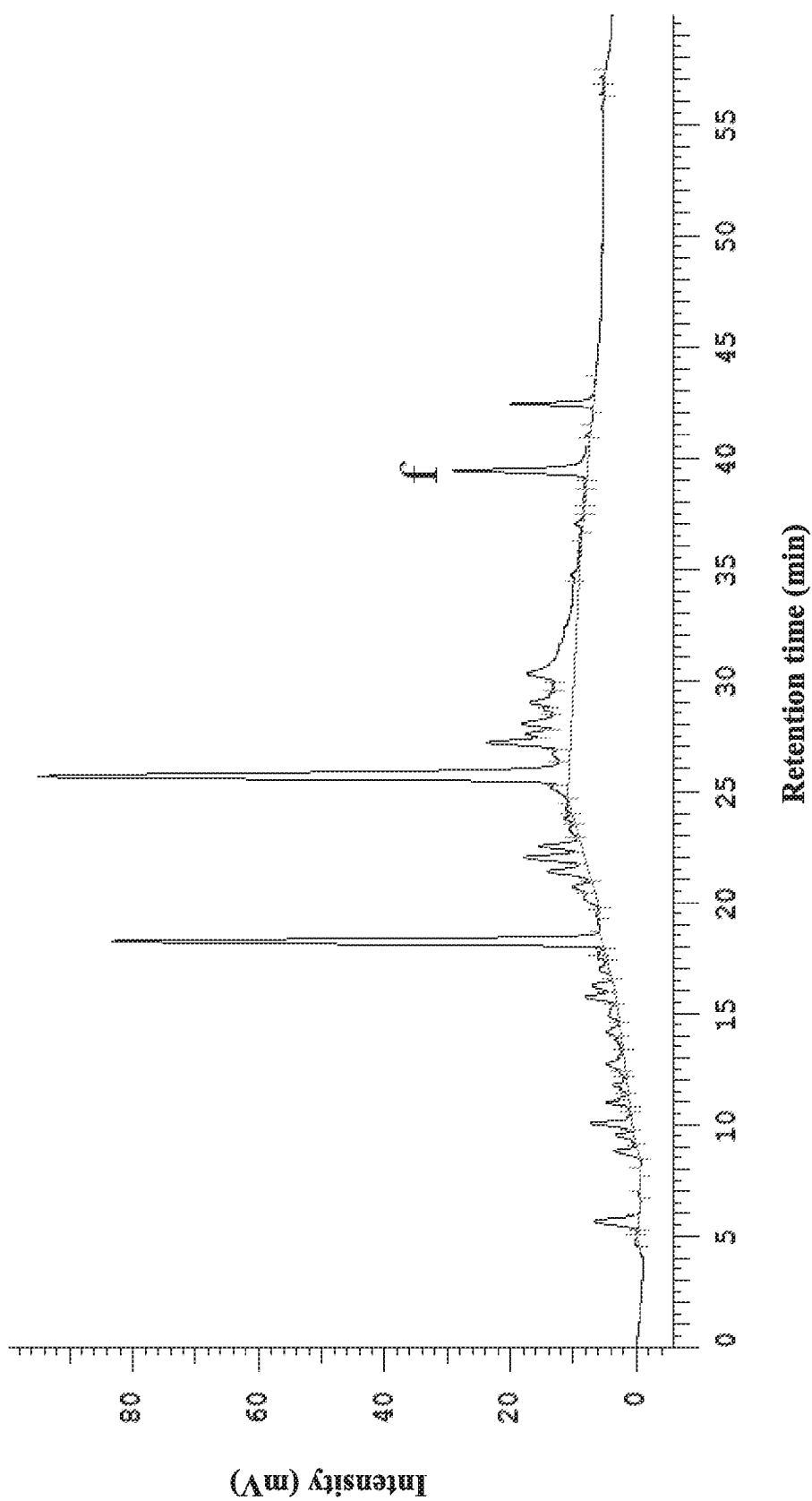
FIG. 1B shows an HPLC chromatogram of the *E. purpurea* water extract at detection wavelength of 260 nm; peak f represents alkamide 8/9 (39.4 nm)

FIG. 1A and FIG. 1B show the HLPC chromatograms of the *E. purpurea* water extract. According to FIGS. 1A-1B and the standard curves for the reference standards including the phenolic compounds and alkamide 8/9 (dissolved in 70% methanol) previously described, a quantitative result was obtained and shown in TABLE 2. From TABLE 2, it is observed that the *E. purpurea* water extract, after being concentrated, contains 8911 µg/mL cichoric acid, 6470 µg/mL caftaric acid, 62 µg/mL alkamides, and 9585 µg/mL polysaccharides.

TABLE 2

| Indicative components | Concentration (µg/mL) |
|---|---|
| Caftaric acid | 6470 |
| Chlorogenic acid | 144 |
| Cynarin | 2507 |
| Echinacoside | 401 |
| Cichoric acid | 8911 |

TABLE 2-continued

| Indicative components | Concentration (μg/mL) |
|---|---|
| Alkamide 8/9 | 62 |
| Polysaccharides | 9585 |

To identify the constituents of the *S. miltiorrhiza* extract, HPLC was used to analyze the indicative components of the 70% ethanol extract of *S. miltiorrhiza* described in Example 1.1. The reference standards include salvianolic acid B, tanshinone I, cryptotanshinone, and tanshinone IIA. While analysis was carried out, the mobile phase (pH 2.77) was a combination of a 0.25% acetic acid aqueous solution and methanol according to the gradient program shown in TABLE 3; the flow rate was 0.5 mL/min; column temperature was 40° C.; and the detection wavelength was 270 nm.

TABLE 3

| | Time (min) | | | | | |
|---|---|---|---|---|---|---|
| | 0 | 25 | 30 | 50 | 60 | 70 |
| 0.25% acetic acid | 60 | 20 | 20 | 0 | 0 | 60 |
| methanol | 40 | 80 | 80 | 100 | 100 | 40 |

Figure 2:
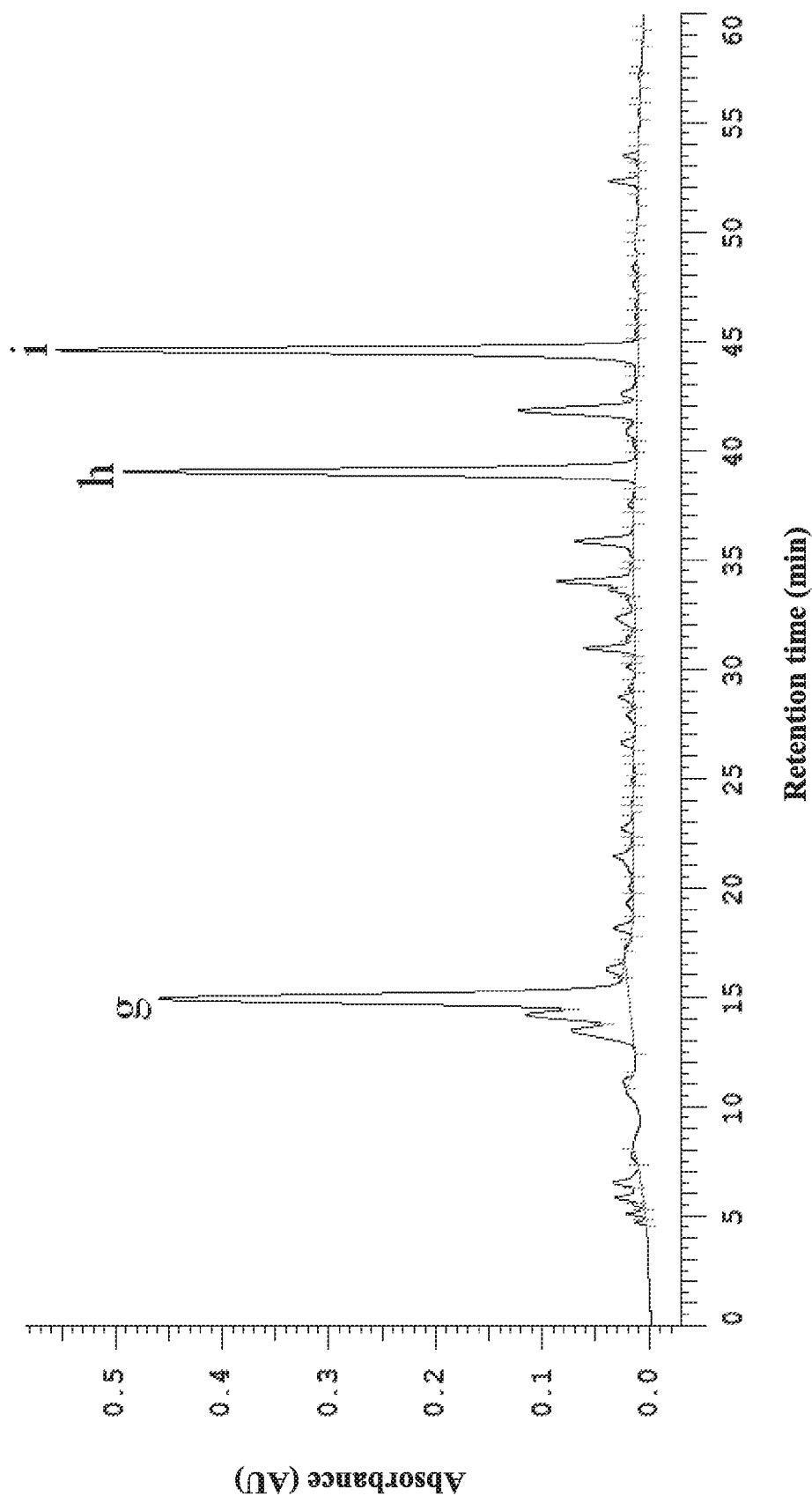
FIG. 2 shows an HPLC chromatogram of a 70% ethanol extract of *S. miltiorrhiza* at detection wavelength of 270 nm; peak g represents salvianolic acid B (14.92 min), peak h represents tanshinone I and cryptotanshinone (39.04 min), and peak i represents tanshinone IIA (44.5 min)

FIG. 2 show the HLPC chromatogram of the 70% ethanol extract of *S. miltiorrhiza*. According to FIG. 2 and the standard curves for the reference standards including salvianolic acids (dissolved in 70% methanol) and tanshinones (dissolved in acetone), a quantitative result was obtained and shown in TABLE 4.

TABLE 4

| Indicative components | Concentration (μg/mL) |
|---|---|
| Salvianolic acid B | 8847.80 ± 94.92 |
| Tanshinone I and Cryptotanshinone | 505.37 ± 13.99 |
| Tanshinone IIA | 714.01 ± 48.71 |

Example 2

Antiviral Activity of the *Echinacea purpurea* Extract and the *Salvia miltiorrhiza* Extract Human adenovirus type 3 (HAdV3) and enterovirus 71 (EV71) are exemplary in this example for description of the antiviral effects of the *E. purpurea* extract and the *S. miltiorrhiza* extract of the present invention. After screening hundreds of plant extracts using plaque assay, it has been shown that the *E. purpurea* extract and the *S. miltiorrhiza* extract possess the best antiviral activity against HAdV3 and EV71.

Figure 3A:
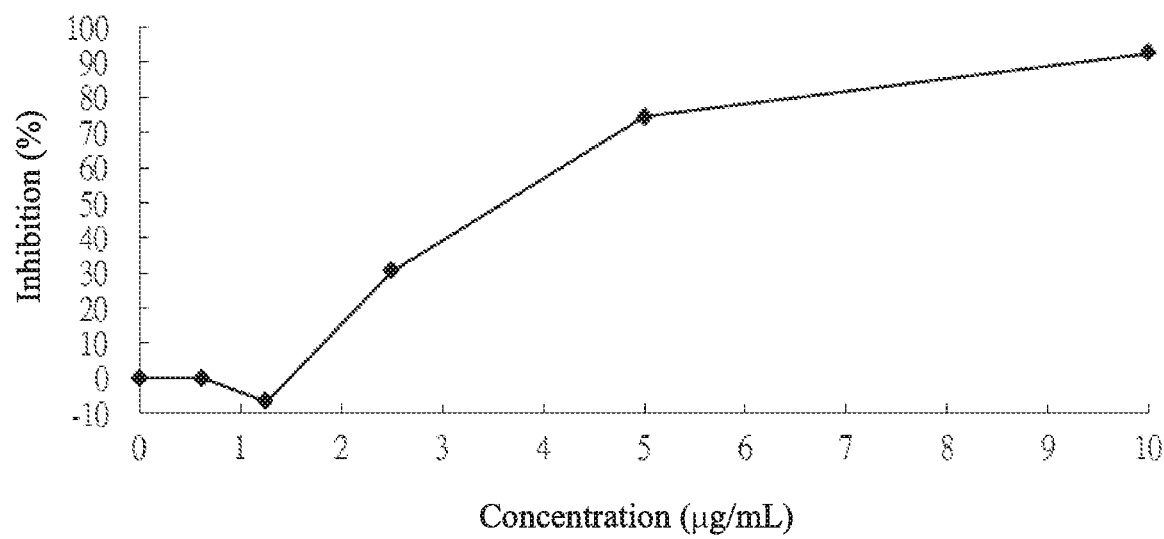
FIG. 3A shows the antiviral effect of a water extract of the aerial part of *E. purpurea* (EPA-W) on human adenovirus type 3 (HAdV3)
Figure 3B:
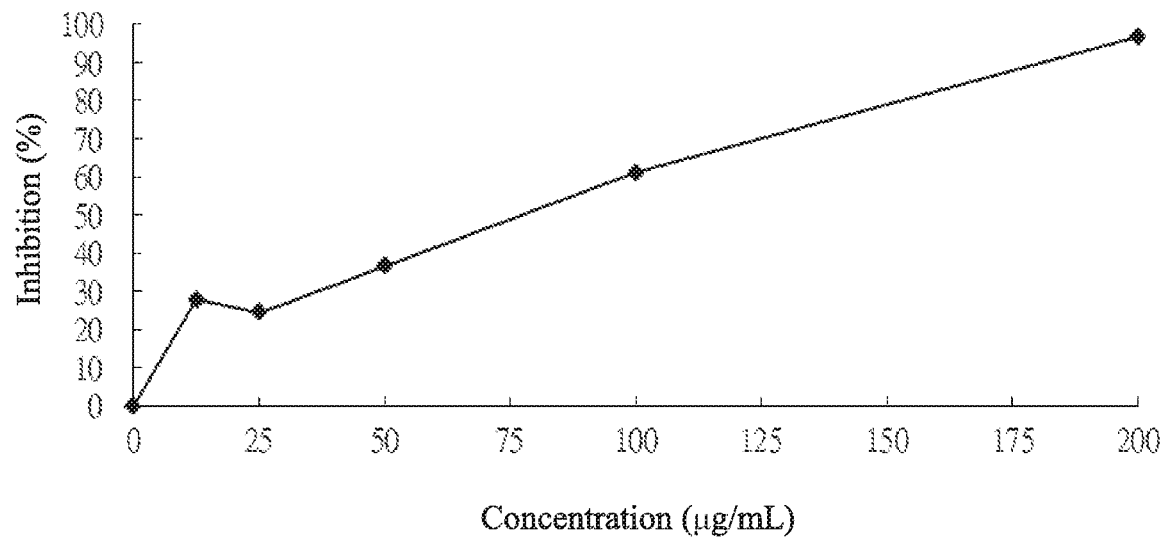
FIG. 3B shows the antiviral effect of EPA-W on enterovirus 71 (EV71)
Figure 3C:
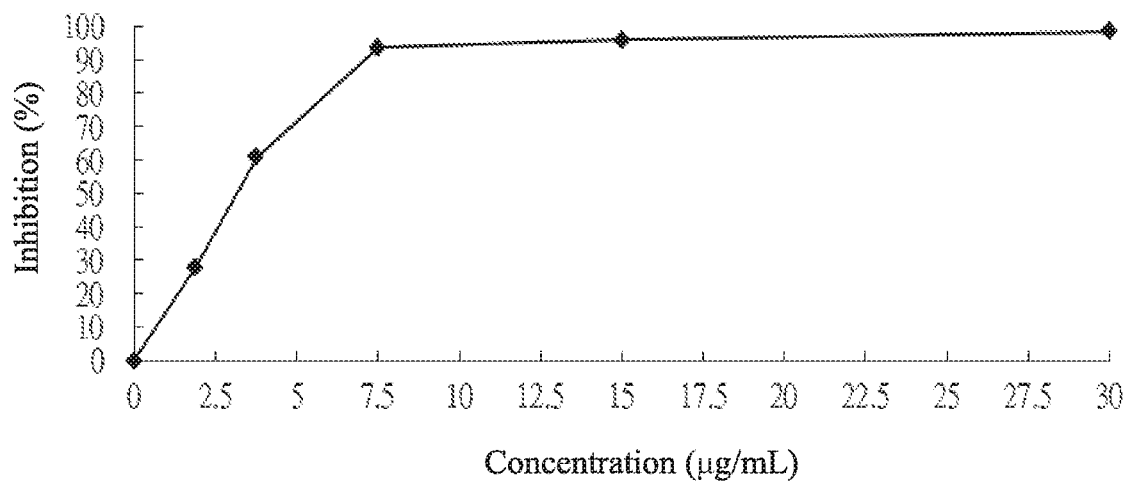
FIG. 3C shows the antiviral effect of a 70% ethanol extract of the root and rhizome of *S. miltiorrhiza* (SMf-2-E) on HAdV3.
Figure 3D:
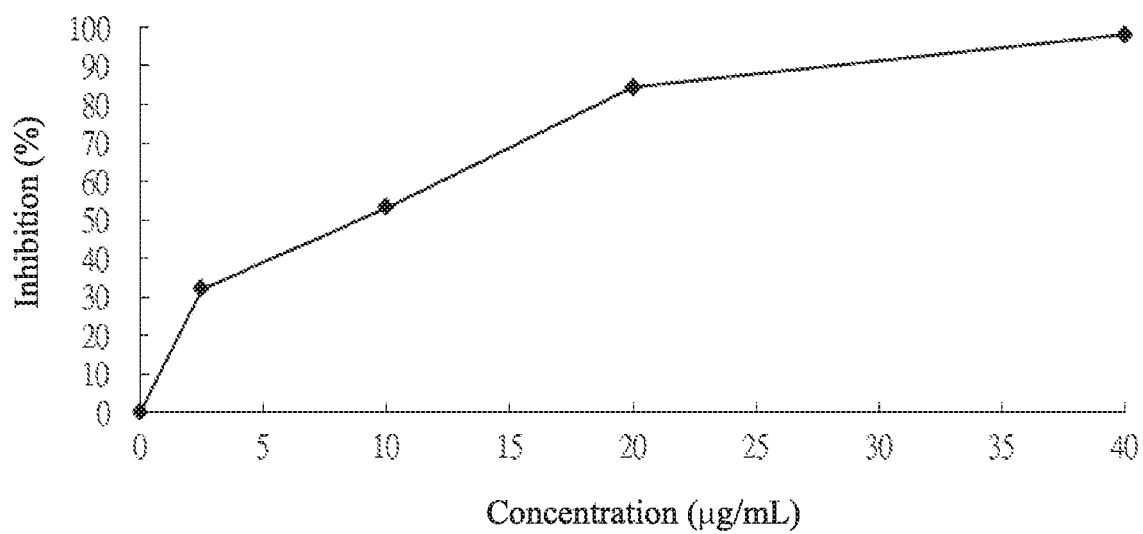
FIG. 3D shows the antiviral effect of SMf-2-E on EV71.

FIGS. 3A and 3B show the antiviral effects of a water extract of the aerial part of *E. purpurea* (abbreviated as EPA-W) on HAdV3 and EV71, respectively. FIGS. 3C and 3D show the antiviral effects of a 70% ethanol extract of the root and rhizome of *S. miltiorrhiza* (abbreviated as SMf-2-E) on HAdV3 and EV71, respectively. The minimal concentrations of these extracts required to reduce the number of viral plaques by 50% and 90%, denoted as IC50 and IC90, respectively, were calculated by regression analysis of the dose-response curves as shown in FIGS. 3A-3D.

TABLE 5 shows the IC50 and IC90 values of various extracts of *E. purpurea* and *S. miltiorrhiza* against HAdV3 and EV71. The *E. purpurea* extracts includes the water extract of the aerial part of *E. purpurea* (EPA-W), a 70% ethanol extract of the aerial part of *E. purpurea* (EPA-E), a 70% ethanol extract of *E. purpurea* root (EPR-E), and a supercritical carbon dioxide extract of *E. purpurea* root (EPR-C). The *S. miltiorrhiza* extracts includes the 70% ethanol extract of the root and rhizome of *S. miltiorrhiza* (SMf-2-E) and a water extract of the root and rhizome of *S. miltiorrhiza* (SMf-2-W). According to TABLE 5, the 70% ethanol extract of the root and rhizome of *S. miltiorrhiza* exhibited the lowest IC50 (3.4 μg/mL) against HAdV3 as well as the lowest IC50 (8.3 μg/mL) against EV71; the water extract of the aerial part of *E. purpurea* exhibited the second lowest IC50 (4.6 μg/mL) against HAdV3 as well as the second lowest IC50 (82.2 μg/mL) against EV71. The results indicated that all the *E. purpurea* extracts and the *S. miltiorrhiza* extracts, regardless of use of water or water-alcohol mixture for extraction, possessed antiviral activity against adenovirus and enterovirus, and that the EPA-W and the SMf-2-E show the highest antiviral activity among these extracts.

TABLE 5

| | Adenovirus serotype 3 | | Enterovirus 71 | |
|---|---|---|---|---|
| Extracts | IC50 (μg/mL) | IC90 (μg/mL) | IC50 (μg/mL) | IC90 (μg/mL) |
| EPA-W | 4.6 | 8.7 | 82.2 | 179.8 |
| EPA-E | 9.9 | 37.2 | 239.9 | 430.8 |
| EPR-E | 26.9 | 47.7 | 300-400 | >400 |
| EPR-C | >1000 | >1000 | >1000 | >1000 |
| SMf-W | 10.9 | 44.5 | 113.0 | 208.3 |
| SMf-2-E | 3.4 | 7.0 | 8.3 | 31.4 |

According to the results of cytotoxicity assay, all the *E. purpurea* extracts in TABLE 5 showed no cytotoxic effect at the concentration of 1500 μg/mL, and all the *Salvia miltiorrhiza* extracts in TABLE 5 showed no cytotoxic effect at the concentration of 200 μg/mL. Therefore, these extracts have high selective indices and can be used to prevent or treat diseases associated with viral infection and to alleviate the disease-related symptoms.

Example 3

Figure 4A:
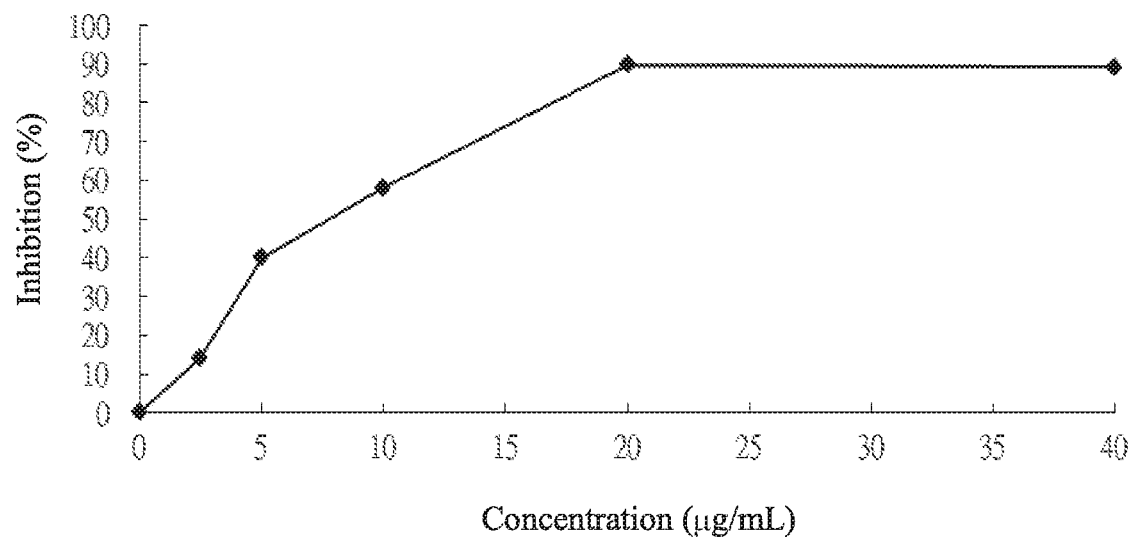
FIG. 4A shows the antiviral effect of an antiviral composition on HAdV3, wherein the antiviral composition contains EPA-W and SMf-2-E at a weight ratio of 3:7.
Figure 4B:
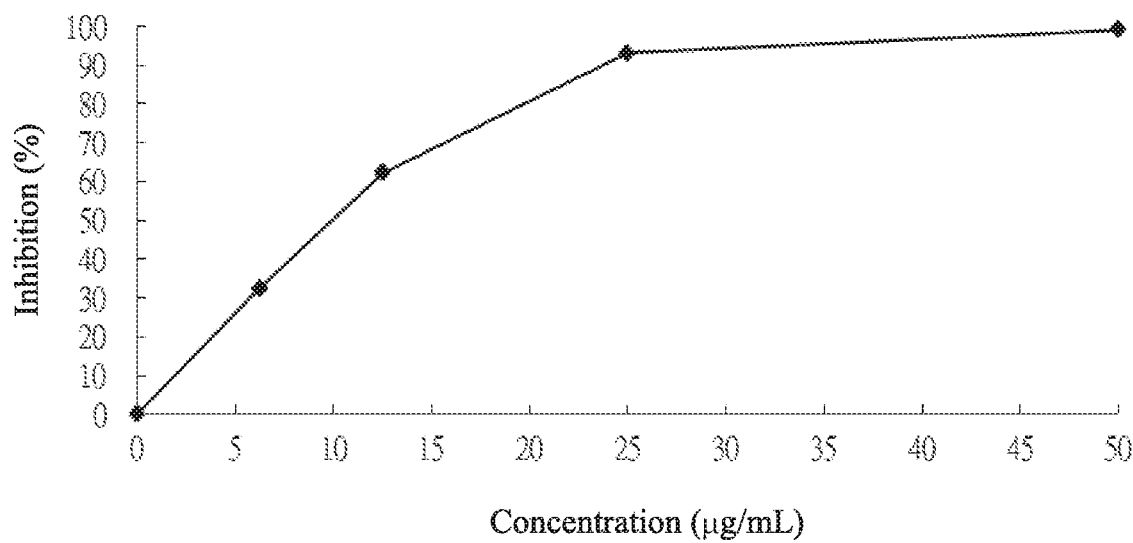
FIG. 4B shows the antiviral effect of the antiviral composition on EV71, wherein the antiviral composition contains EPA-W and SMf-2-E at a weight ratio of 3:7.

Antiviral Activity of a Composition Containing the *E. purpurea* Extract and the *S. miltiorrhiza* Extract The antiviral activity of combinations of the *E. purpurea* water extract and the *S. miltiorrhiza* ethanol extract at different ratios was further investigated by plaque assay. TABLE 6 shows the antiviral effects of the compositions containing EPA-W and SMf-2-E at various ratios. According to TABLE 6, when EPA-W and SMf-2-E were mixed at a weight ratio ranging from 1:9 to 9:1, the resulting compositions exhibited considerably low IC50 and IC90 values against HAdV3 and EV71. FIG. 4A and FIG. 4B show the anti-HAdV3 and anti-EV71 activity of an antiviral composition prepared by mixing EPA-W and SMf-2-E at a weight ratio of 3:7. As shown in TABLE 6, this composition had the lowest IC50 and IC90 values against EV71, and also had the second lowest IC50 and the lowest IC90 values against HAdV3. The results indicated that the mixing of the *E. purpurea* water extract and the *S. miltiorrhiza* ethanol extract at specific ratios produced the antiviral composition possessing highly inhibitory effects against both adenovirus and enterovirus.

TABLE 6

| Weight ratio of EPA-W:SMf-2-E | Human adenovirus type 3 | | Enterovirus 71 | |
|---|---|---|---|---|
| | IC50 (µg/mL) | IC90 (µg/mL) | IC50 (µg/mL) | IC90 (µg/mL) |
| 1:9 | 15.6 | 33.2 | 11.5 | 24.2 |
| 3:7 | 9.2 | 19.2 | 10.6 | 23.3 |
| 5:5 | 9.0 | 18.4 | 15.4 | 39.8 |
| 7:3 | 4.1 | 19.8 | 17.9 | 45.0 |
| 9:1 | 8.6 | 21.3 | 25.0 | 87.7 |

Example 4

Anti-Adenovirus Activity of a Composition Containing the E. purpurea Extract and the S. miltiorrhiza Extract The antiviral activity of a combination of the E. purpurea water extract and the S. miltiorrhiza ethanol extract against various adenoviruses was evaluated by plaque assay. TABLE 7 shows the antiviral effects of the antiviral composition, which contains EPA-Wand SMf-2-E at a weight ratio of 3:7, on human adenovirus types 1, 2, 3, 4, and 7. According to TABLE 7, this composition exhibited considerably low IC50 and IC90 values against all the tested human adenoviruses, again indicating that the mixing of the E. purpurea water extract and the S. miltiorrhiza ethanol extract at specific ratios produced the antiviral composition possessing highly inhibitory effects against adenoviruses.

TABLE 7

| Type of adenovirus | IC50 (µg/mL) | IC90 (µg/mL) |
|---|---|---|
| Human adenovirus type 1 (HAdV1) | 12.3 | 20-40 |
| Human adenovirus type 2 (HAdV2) | 10.8 | 20-40 |
| Human adenovirus type 3 (HAdV3) | 9.2 | 19.2 |
| Human adenovirus type 4 (HAdV4) | 8.1 | 29.7 |
| Human adenovirus type 7 (HAdV7) | 6.2 | 40-80 |

Example 5

Virucidal Effects of the E. purpurea Extract and the S. miltiorrhiza Extract

The antiviral mechanisms of the E. purpurea extract and the S. miltiorrhiza extract were further studied in the following Examples 5-7. HAdV3 and EV71 are exemplary in this example for description of the virucidal effects, estimated by virucidal assay, of the E. purpurea extract and the S. miltiorrhiza extract. For experimentation, a virus solution containing $10^6$ PFU of HAdV3 or $10^7$ PFU of EV71 was mixed with various concentrations of EPA-W or SMf-2-E for 2 hours at 37° C. The residual viral infectivity of each of the mixtures was then determined by plaque assay.

Figure 5A:
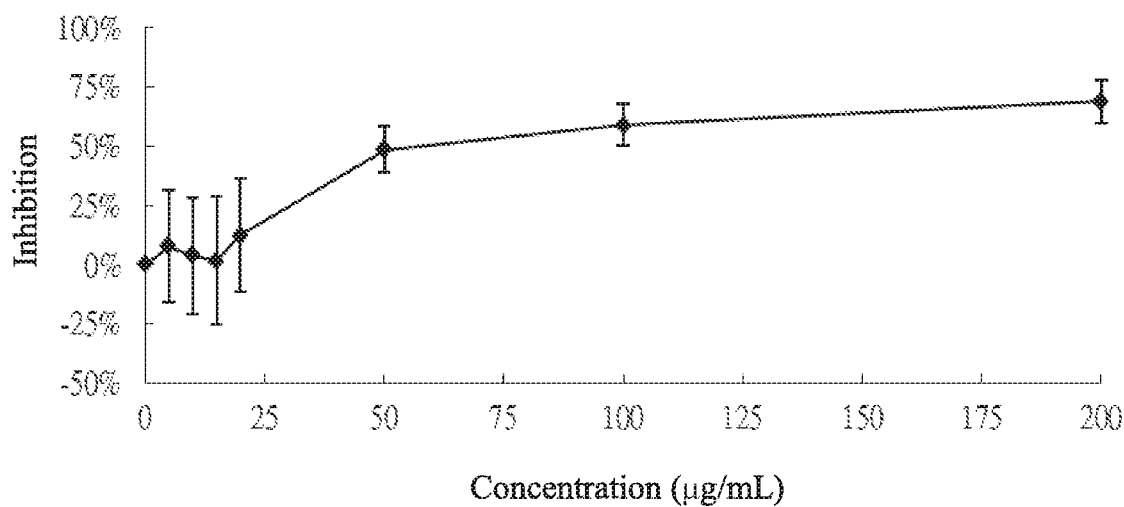
FIG. 5A shows the virucidal activity of EPA-W against HAdV3.
Figure 5B:
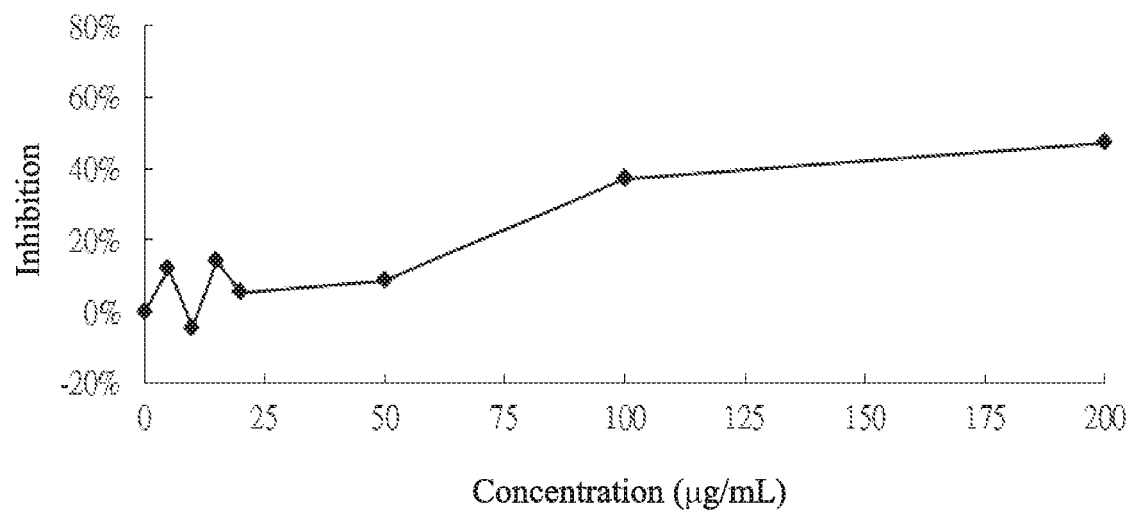
FIG. 5B shows the virucidal activity of SMf-2-E against HAdV3.

FIGS. 5A-5B show the virucidal activity of EPA-W and SMf-2-E against HAdV3. According to FIG. 5A, EPA-W had a virucidal effect on HAdV3 at a concentration of 50 µg/mL or above. According to FIG. 5B, SMf-2-E had a virucidal effect on HAdV3 at a concentration of 100 µg/ml or above. Given that the IC50 of EPA-W against HAdV3 was 4.6 µg/mL and that of SMf-2-E against HAdV3 was 3.4 µg/mL (TABLE 5), these results showed that the S. miltiorrhiza extract had little virucidal effect on HAdV3, and the E. purpurea extract had some virucidal effect on HAdV3.

Figure 5C:
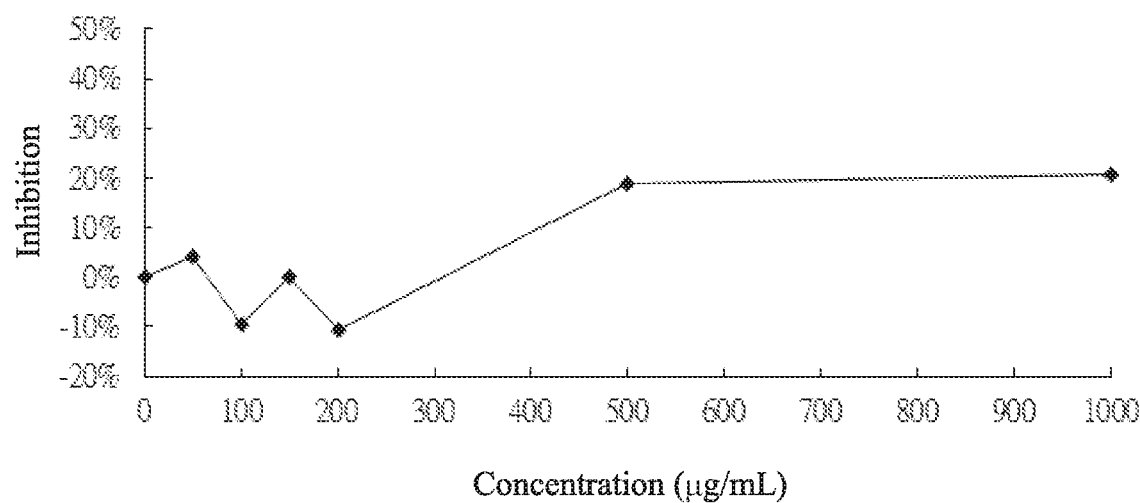
FIG. 5C shows the virucidal activity of EPA-W against EV71.
Figure 5D:
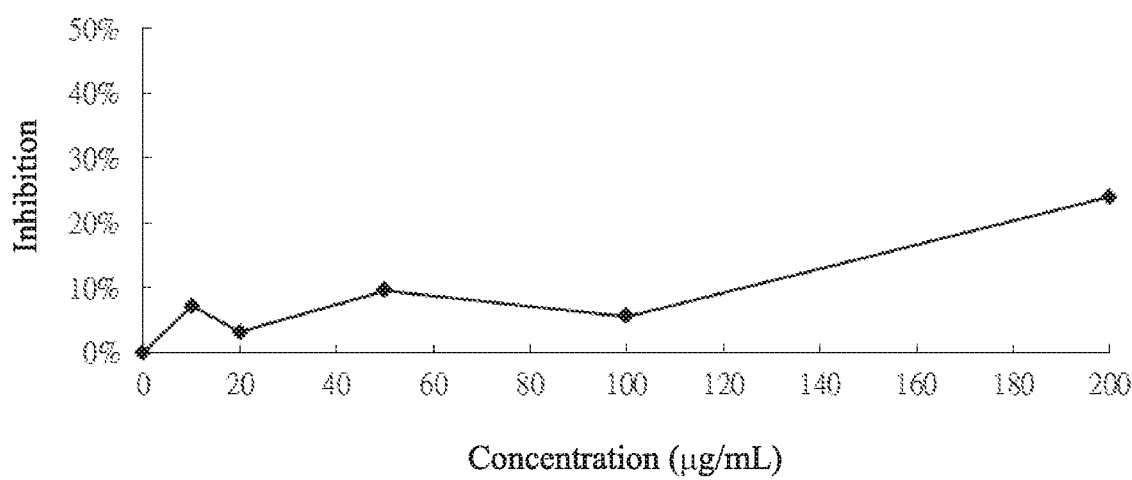
FIG. 5D shows the virucidal activity of SMf-2-E against EV71.

FIGS. 5C-5D show the virucidal activity of EPA-W and SMf-2-E against EV71. According to FIGS. 5C-5D, EPA-W at a concentration of up to 1000 µg/mL and SMf-2-E at a concentration of up to 200 µg/mL had no virucidal effect on EV71. Given that the IC50 of EPA-W against EV71 was 82.2 µg/mL and that of SMf-2-E against EV71 was only 8.3 µg/mL (TABLE 5), these results revealed that the antiviral effects of the E. purpurea and S. miltiorrhiza extracts against EV71 were not caused by direct virucidal activity.

Example 6

Effects of the E. purpurea Extract and the S. miltiorrhiza Extract on Virus Attachment HAdV3 and EV71 are exemplary in this example for description of the effects of the E. purpurea extract and the S. miltiorrhiza extract on virus attachment or adsorption to host cells. Attachment assay was performed and the results were shown in FIGS. 6A-6D. For the HAdV3 attachment assay, 200 PFU/well HAdV3 was used to inoculate the Vero cell monolayer in the absence or presence of serial dilutions of EPA-W or SMf-2-E. For the EV71 attachment assay, 100 PFU/well EV71 was used to inoculate the Vero cell monolayer in the absence or presence of serial dilutions of EPA-W or SMf-2-E.

Figure 6A:
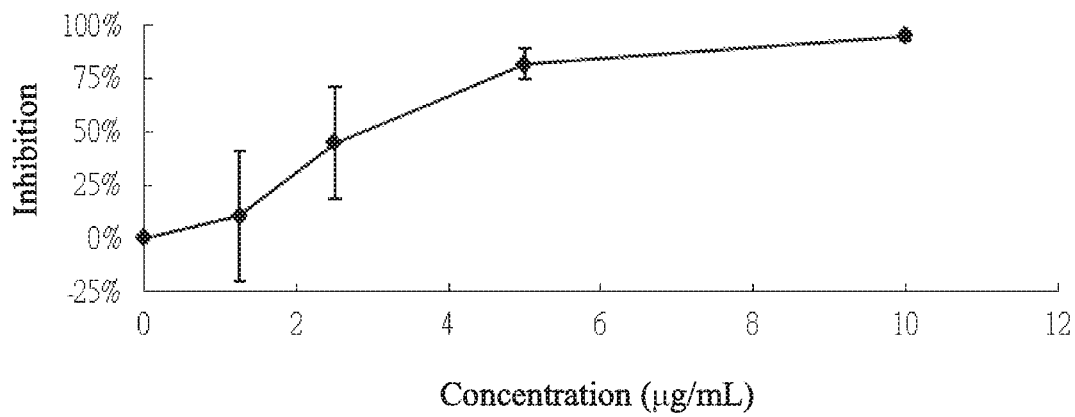
FIG. 6A shows the inhibitory effect of EPA-W on HAdV3 attachment to Vero cells.
Figure 6B:
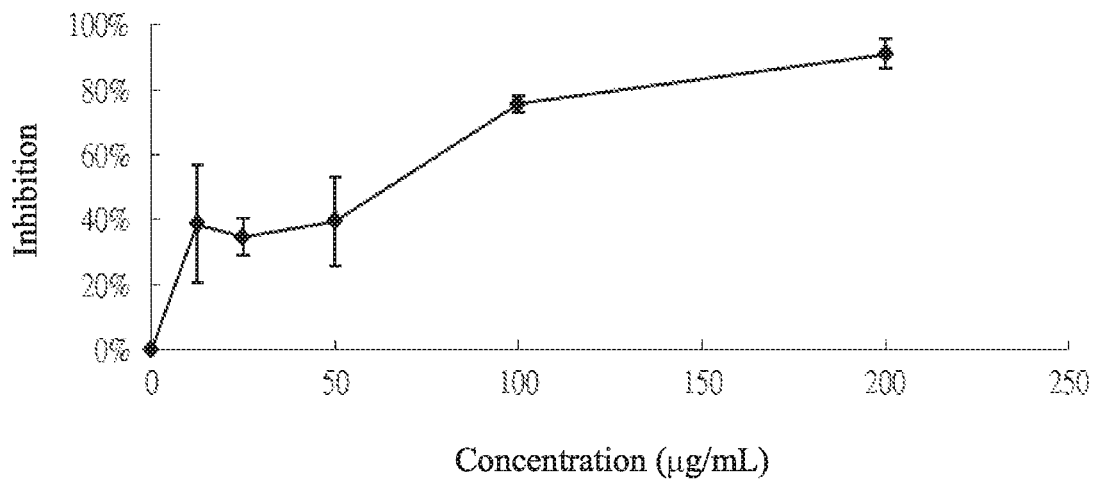
FIG. 6B shows the inhibitory effect of EPA-W on EV71 attachment to Vero cells.
Figure 6C:
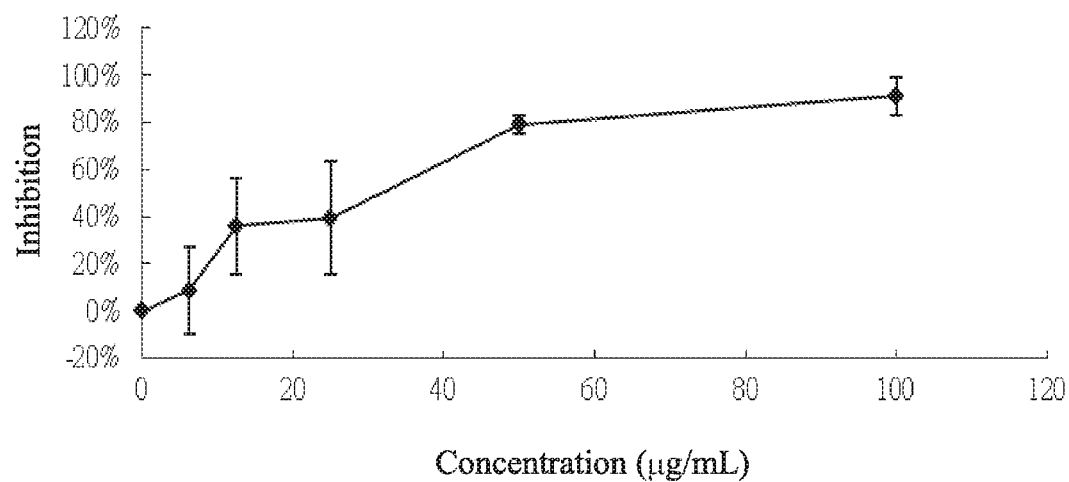
FIG. 6C shows the inhibitory effect of SMf-2-E on HAdV3 attachment to Vero cells.
Figure 6D:
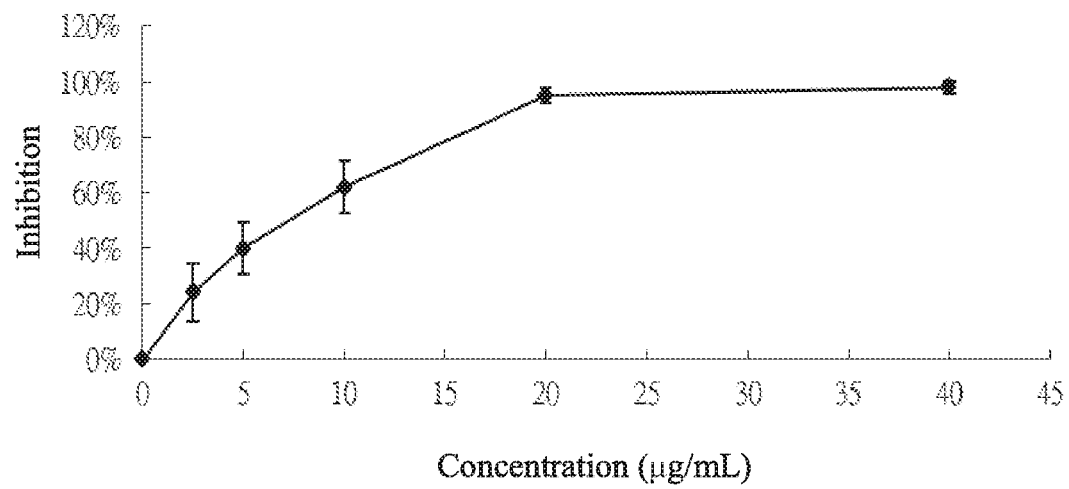
FIG. 6D shows the inhibitory effect of SMf-2-E on EV71 attachment to Vero cells.

According to FIGS. 6A-6B, EPA-W prevented the attachment of HAdV3 and EV71 to Vero cells. According to FIGS. 6C-6D, SMf-2-E exhibited mild inhibitory effect on the attachment of HAdV3 to Vero cells but prevented the attachment of EV71. The results indicated that both the E. purpurea extract and the S. miltiorrhiza extract inhibited adenovirus and enterovirus attachment to cells and possessed potent antiviral activity.

Example 7

Effect of the E. purpurea Extract and the S. miltiorrhiza Extract on Virus Penetration HAdV3 and EV71 are exemplary in this example for description of the effects of the E. purpurea extract and the S. miltiorrhiza extract on virus penetration or entry to host cells. Penetration assay was carried out in this study. According to FIGS. 5A-5D, EPA-W at 20 µg/mL and SMf-2-E at 50 µg/mL had no significant virucidal effect on HAdV3, and EPA-W at 1000 µg/mL and SMf-2-E at 200 µg/mL had no significant virucidal effect on EV71. Thus, for the HAdV3 penetration assay, EPA-W was used at a concentration of no more than 20 µg/mL and SMf-2-E was used at a concentration of no more than 50 µg/mL. Similarly, for the EV71 penetration assay, EPA-W was used at a concentration of no more than 1000 µg/mL and SMf-2-E was used at a concentration of no more than 200 µg/mL. The HAdV3 at 200 PFU or EV71 at 100 PFU was used to infect Vero cells in the penetration assay.

Figure 7A:
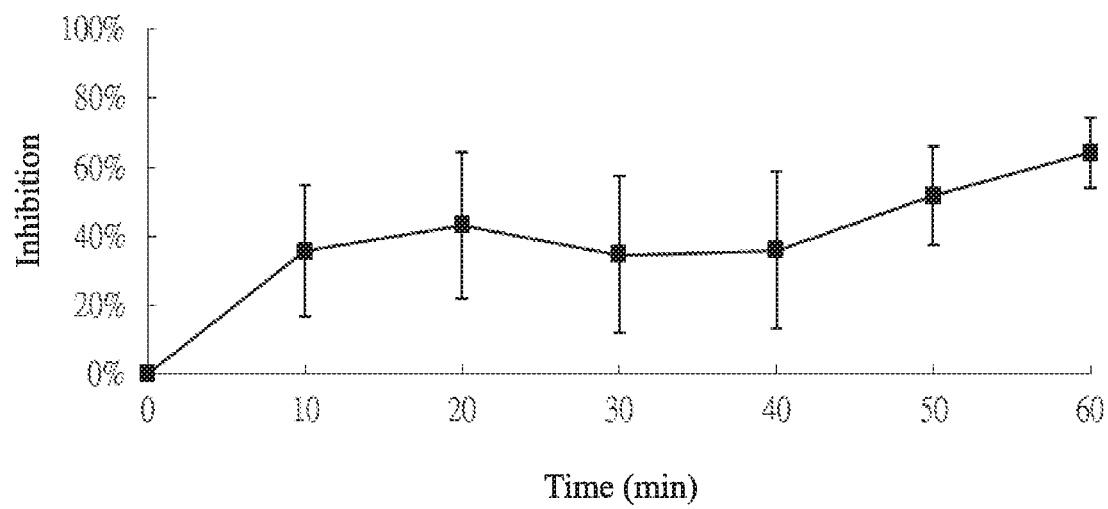
FIG. 7A shows the inhibitory effect of EPA-W (10 μg/mL) on HAdV3 penetration into Vero cells.
Figure 7B:
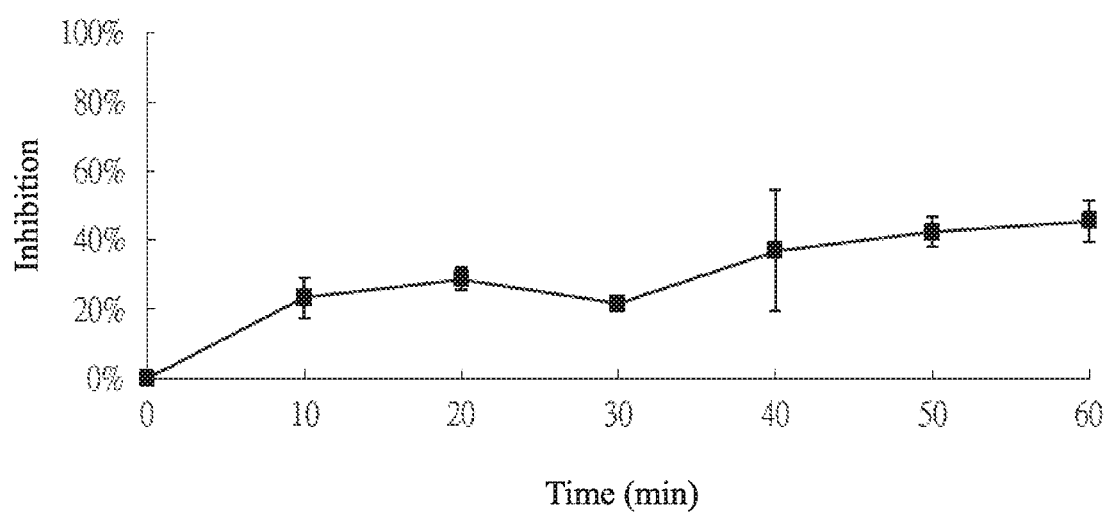
FIG. 7B shows the inhibitory effect of EPA-W (200 μg/mL) on EV71 penetration into Vero cells.
Figure 7C:
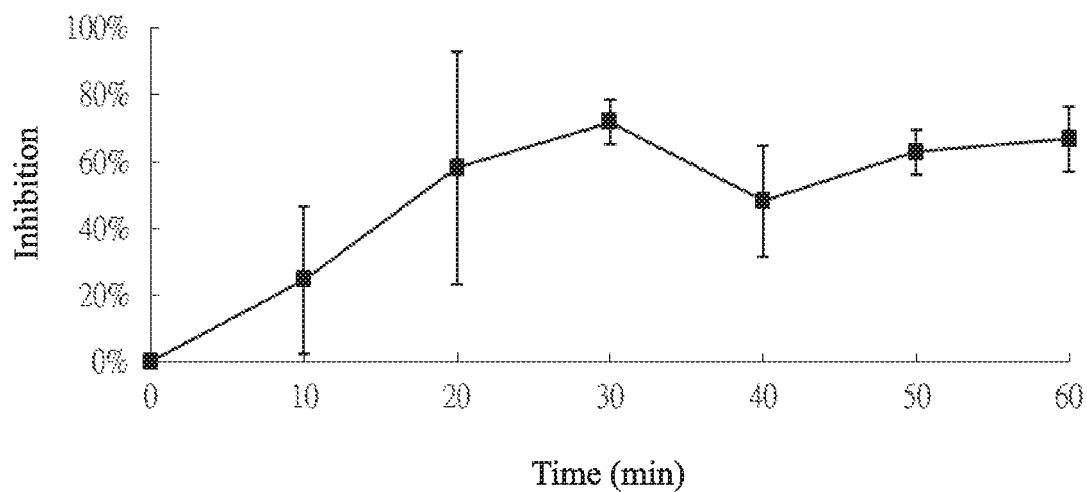
FIG. 7C shows the inhibitory effect of SMf-2-E (10 μg/mL) on HAdV3 penetration into Vero cells.
Figure 7D:
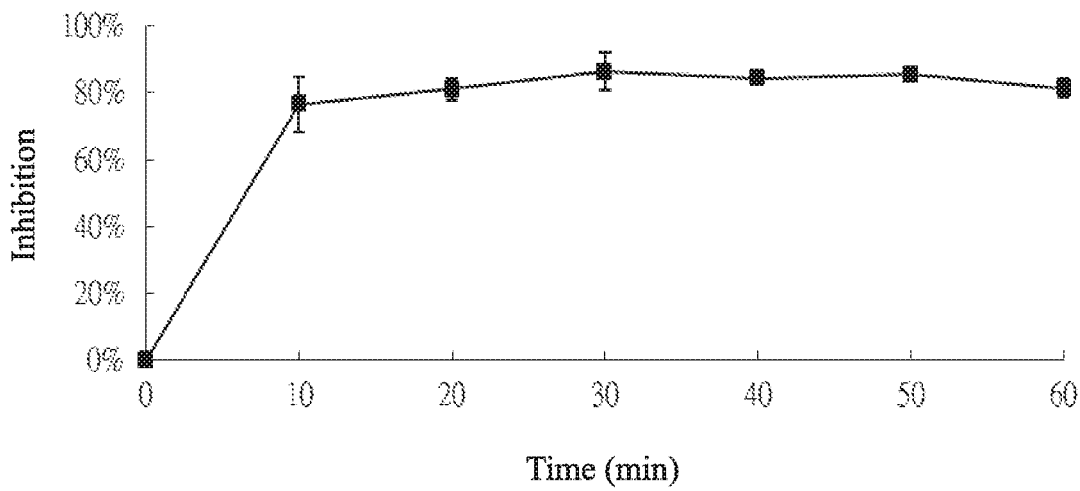
FIG. 7D shows the inhibitory effect of SMf-2-E (50 μg/mL) on EV71 penetration into Vero cells.

FIGS. 7A and 7B show the inhibitory effects of EPA-W on penetration of HAdV3 and EV71 into cells while at concentrations of 10 µg/mL and 200 µg/mL, respectively. FIGS. 7C and 7D show the inhibitory effects of SMf-2-E on penetration of HAdV3 and EV71 into cells while at concentrations of 10 µg/mL and 50 µg/mL, respectively. The inhibitory effect of each of the extracts on virus penetration was determined by observation of the effect within 10 minutes after the extract was added to the cells. According to FIG. 7A, EPA-W exhibited partial inhibition (about 35%) on HAdV3 penetration. According to FIG. 7C, SMf-2-E also exhibited partial inhibition on HAdV3 penetration. According to FIG. 7D, SMf-2-E was able to prevent the penetration of EV71, and the inhibitory effect (about 80%) on virus penetration was observed as early as 10 minutes after SMf-2-E was added. The results indicated that both the E. purpurea extract and the S. miltiorrhiza extract exerted antiviral activity through inhibiting adenovirus or enterovirus penetration or entry into cells.

In view of the data disclosed in examples 5-7, the antiviral mechanism of the *E. purpurea* extract against adenovirus is mainly through inhibiting viral attachment and somewhat through virucidal effect and inhibiting viral penetration, and its antiviral mechanism against enterovirus is mainly through inhibiting viral attachment. The antiviral mechanism of the *S. miltiorrhiza* extract against enterovirus is mainly through inhibiting viral penetration and somewhat through inhibiting viral attachment, and its antiviral mechanism against adenovirus is also through inhibiting viral attachment and penetration.

In conclusion, the present invention discloses that the antiviral composition, prepared from the *E. purpurea* extract, the *Salvia miltiorrhiza* extract, or combinations thereof, effectively inhibits adenovirus and enterovirus infection. The antiviral composition reduces adenovirus and enterovirus infection rates through virucidal activity against adenovirus and inhibition of adenovirus and enterovirus attachment to and penetration into cells, and it has the potential for preventing or treating diseases associated with viral infection in a subject in need. Therefore, the methods of the present invention for treating or preventing viral infection and for preparing the antiviral composition have obvious commercial value.

REFERENCES

Cheng H Y, Lin T C, Yang C M, Wang K C, Lin L T, Lin C C. Putranjivain A from *Euphorbia jolkini* inhibits both virus entry and late stage replication of herpes simplex virus type 2 in vitro. The Journal of antimicrobial chemotherapy 2004 April: 53:577-583.

What is claimed is:

1. A method of treating or preventing a viral infection, comprising:
administering to a subject in need thereof an effective amount of an antiviral composition, wherein the antiviral composition consists essentially of an aqueous *Echinacea purpurea* extract and alcohol *Salvia miltiorrhiza* extract;
wherein the viral infection is caused by an adenovirus, an enterovirus, or combinations thereof:
wherein the enterovirus is enterovirus 71, and the adenovirus is selected from the group consisting of human adenovirus type 1, human adenovirus type 2, human adenovirus type 3, human adenovirus type 4, and human adenovirus type 7;
wherein the aqueous *Echinacea purpurea* extract inhibits attachment of the adenovirus or the enterovirus to a cell;
wherein the alcohol *Salvia miltiorrhiza* extract inhibits attachment of the adenovirus or the enterovirus to the cell;
wherein the aqueous *Echinacea purpurea* extract is prepared by extracting an aerial part or root of *Echinacea purpurea*; and
wherein the alcohol *Salvia miltiorrhiza* extract is prepared by extracting a root or rhizome of *Salvia miltiorrhiza*.

2. The method of claim 1, wherein the alcohol comprises 1-95% v/v ethanol.

3. The method of claim 1, wherein the *S. miltiorrhiza* extract is prepared by extraction with a 70% ethanol aqueous solution, and the antiviral composition comprises the *E. purpurea* extract and the *S. miltiorrhiza* extract at a weight ratio ranging from 1:9 to 9:1.

4. The method of claim 3, wherein the antiviral composition comprises the *E. purpurea* extract and the *S. miltiorrhiza* extract at a weight ratio of 3:7.

5. The method of claim 1, wherein the *E. purpurea* extract inhibits penetration of the adenovirus into a cell.

6. The method of claim 1, wherein the *E. purpurea* extract deactivates the adenovirus.

7. The method of claim 1, wherein the *S. miltiorrhiza* extract inhibits penetration of the adenovirus or the enterovirus into a cell.

* * * * *